United States Patent [19]
Kuroita et al.

[11] Patent Number: 5,990,302
[45] Date of Patent: Nov. 23, 1999

[54] METHOD FOR ISOLATING RIBONUCLEIC ACID

[75] Inventors: Toshihiro Kuroita; Hideki Kamimura; Bunsei Kawakami; Yoshihisa Kawamura, all of Tsuruga, Japan

[73] Assignee: Toyo Boseki Kabushiki Kaisha, Osaka, Japan

[21] Appl. No.: 08/893,561

[22] Filed: Jul. 11, 1997

[30] Foreign Application Priority Data

Jul. 12, 1996 [JP] Japan ..................... 8-183381

[51] Int. Cl.$^6$ ............. C07H 21/00; C12Q 1/68; C12N 15/00
[52] U.S. Cl. ............. 536/25.4; 435/6; 435/91.1; 435/91.3; 935/76; 935/77; 935/78; 536/23.1; 536/24.3
[58] Field of Search ............. 435/6, 91.1, 91.3; 536/23.1, 24.3, 25.4; 935/76, 77, 78

[56] References Cited

U.S. PATENT DOCUMENTS

| | | | |
|---|---|---|---|
| 5,128,247 | 7/1992 | Koller | 435/91 |
| 5,155,018 | 10/1992 | Gillespie et al. | 43/91 |
| 5,523,231 | 6/1996 | Reeve | 435/270 |
| 5,620,852 | 4/1997 | Lin et al. | 435/6 |
| 5,728,822 | 3/1998 | Macfarlane | 536/25.41 |

FOREIGN PATENT DOCUMENTS

| | | |
|---|---|---|
| 0 389 063 | 9/1990 | European Pat. Off. |
| 92/18514 | 10/1992 | WIPO. |
| 95/34569 | 12/1995 | WIPO. |
| 96/18731 | 6/1996 | WIPO. |

OTHER PUBLICATIONS

Chomczyneski et al., "Single–Step Method Of RNA Isolation By Acid Guanidinium Thiocyante–Phenol–Chloroform Extraction", *Analytical Biochemistry*, vol. 162:156–159, (1987).

Boom et al., "Rapid And Simple Method For Purification Of Nucleic Acids", *Journal of Clinical Microbiology*, vol. 28(3):495–503, (1990).

Vogelstein et al., "Preparative And Analytical Purification Of DNA From Agarose", *Proc. Natl. Acad. Sci. USA*, vol. 76(2):615–619, (1979).

Purification of Plasmid DNA, *Molecular Cloning*, 2nd ed., pp. 1. 40 and 1.41, (1989).

Okamoto et al., "Detection Of Hepatitis C Virus RNA By A Two–Stage Polymerase Chain Reaction With Two Pairs Of Primers Deduced from the 5'–Noncoding Region", *Japan, J. Exp. Med.*, vol. 60(4):215–222, (1990).

Pairs Of Primers Deducted from the 5'–Noncoding Region, *Japan, J. Exp. Med.*, vol. 60(4):215–222, (1990).

Dahle et al., BioTechniques 15(6) : 1102–1105 (1993).

Chirgwin et al., Biochemistry 18(24) : 5294–5299 (1979).

Krawetz et al., J. of Biochemical and Biophysical Methods 12 : 29–36(1986).

Davis et al., "Basic Methods in Molecular Biology", pp. 129–142, Elsevier Publishing (1986).

The Dynal Technical Handbook, 2nd Edition, pp. 35–60, Dynal A.S, Oslo, Norway (1995).

*Primary Examiner*—W. Gary Jones
*Assistant Examiner*—Ethan Whisenart
*Attorney, Agent, or Firm*—Foley & Lardner

[57] ABSTRACT

A method for isolating a ribonucleic acid, which comprises dissolution of a sample containing the ribonucleic acid, such as cells, in an acidic solution containing a lithium salt and a chaotropic agent, bringing the ribonucleic acid into contact with a nucleic acid-binding carrier such as silica particles, thereby to allow selective adsorption of the ribonucleic acid alone onto said carrier, and eluting the ribonucleic acid from the nucleic acid-bound carrier; a reagent therefor; and a method for producing a cDNA from the ribonucleic acid isolated by this method. According to the present invention, a high purity ribonucleic acid can be isolated quickly and safely from a sample containing the ribonucleic acid.

26 Claims, 3 Drawing Sheets

1 2 3

← objective amplification product

METHOD FOR ISOLATING RIBONUCLEIC ACID

TECHNICAL FIELD OF THE INVENTION

The present invention relates to a method for isolating a ribonucleic acid and a reagent therefor. More particularly, the present invention relates to a method for isolating a ribonucleic acid with high purity in a simple and convenient manner from a sample containing said ribonucleic acid by the use of a nucleic acid-binding carrier, and to a reagent therefor. The present invention can be also applied to an automatic nucleic acid extraction device.

BACKGROUND OF THE INVENTION

A deoxyribonucleic acid (DNA) constitutes the genome carrying the information of life. A ribonucleic acid (RNA) is an important biological polymer which receives such information and is involved in protein biosynthesis and the like in the body. The ribonucleic acid is largely divided into a messenger RNA (mRNA), a transfer RNA (tRNA) and a ribosomal RNA (rRNA), and each has distinct properties. There are some viruses that utilize a ribonucleic acid as the genome carrying the information of life.

An analysis of ribonucleic acid provides extremely important information for the fields of biochemistry, genetic engineering, clinical diagnostics and the like. Isolation of ribonucleic acid from a biological material is an essential step for such analysis. It is necessary to use a ribonucleic acid having a highest possible purity to achieve good results in analyses, such as northern blot analysis, reverse transcription-polymerase chain reaction (RT-PCR) and the like, which are routinely used in these fields.

In generality, a ribonucleic acid cannot be extracted without rupture of cells, during which stage a ribonucleic acid is obtained in a mixture with protein, lipid, sugar, deoxyribonucleic acid and the like. Inasmuch as ribonucleic acid is easily degraded by a ribonuclease universally found in living organisms, it is isolated in the presence of a protein denaturing agent or in an organic solvent, thereby weakening the activity of the ribonuclease. The most predominantly used for this end is a so-called AGPC method (Analytical Biochemistry, 162: 156–159 (1987)), which comprises (1) extracting a biological material with a guanidine thiocyanate solution, successively adding an acidic solution, a phenol solution and a chloroform solution, (2) centrifuging the resulting mixture to separate proteins denatured with phenol and insolubilized deoxyribonucleic acids, into an intermediate layer between an organic layer and an aqueous layer, (3) adding isopropanol to the aqueous layer to insolubilize a ribonucleic acid therein, and (4) selectively precipitating the ribonucleic acid alone by centrifugation. The AGPC method is advantageous in that it can isolate ribonucleic acid relatively easily and efficiently, as compared to other methods involving ultracentrifugation for isolating ribonucleic acid. However, it requires a poisonous substance such as phenol and chloroform, as well as a rather time-consuming step such as isopropanol precipitation, which in turn gives rise to a need of a safer and time-saving method when a number of samples are to be treated at the same time in common research institutions.

In the meantime, a different, simple and convenient method for extraction of nucleic acid has been proposed by Boom et al. (J. Clin. Microbiol., 28(3):495–503 (1990)), which uses silica particles as a nucleic acid-binding carrier. This method includes (1) mixing a biological material, a neutral solution consisting of guanidine thiocyanate, EDTA and Triton X-100, and a nucleic acid-binding solid phase (silica) to bind the nucleic acid to said solid phase, (2) separating the nucleic acid-bound solid phase from a liquid phase, (3) washing said solid phase with a wash solution containing guanidine thiocyanate, (4) washing said solid phase with 70% ethanol, (5) washing the solid phase with acetone, followed by drying thereof, and (6) eluting the nucleic acid with an eluent. This method characteristically permits isolation of nucleic acid without the use of a poison such as phenol, or concentration with isopropanol. The ribonucleic acid obtained by this method contains a large amount of deoxyribonucleic acid, which renders this method unsuitable for isolation of ribonucleic acid at high purities.

As a different isolation method of nucleic acid using a carrier such as silica particles, there has been known a method comprising adsorbing a nucleic acid in an agarose gel onto the surface of glass particles in an NaI solution and separating the nucleic acid from a liquid phase (Proc. Natl. Acad. Sci. USA, 76: 615 (1979)). What is common to these methods is that silica and nucleic acid are bound in a neutral solution containing a chaotropic ion (i.e., monovalent anion having greater ionic radius), such as iodide ion and thiocyanate ion. These methods, however, mainly aim at isolation of deoxyribonucleic acid, wherein ribonucleic acid may be isolated yet only in low yields, and isolation of ribonucleic acid alone is not attainable. Again, these methods are unsuitable for isolation of ribonucleic acid.

Another isolation method (lithium precipitation method) of ribonucleic acid has been reported, which utilizes a chemical property that addition of a lithium ion to an aqueous ribonucleic acid solution leads to insolubilization of ribonucleic acid (Molecular Cloning, 2nd ed., 1.40 (1989)). This method, nevertheless, requires centrifugation at high rpm to precipitate ribonucleic acid. Thus, development of an isolation method of ribonucleic acid which is free of such difficulties has been desired.

SUMMARY OF THE INVENTION

It is therefore an object of the present invention to provide a method for quickly and safely isolating a ribonucleic acid with high purity in a simple and convenient manner from a sample such as cells, and a reagent therefor.

As a result of various investigations, there has now been provided a method comprising dissolution of a biological material such as cells in an acidic solution containing a lithium salt and a chaotropic agent and bringing same into contact with a nucleic acid-binding carrier such as silica particles, thereby to greatly increase the yield and purity (i.e., selectivity) of the isolated ribonucleic acid.

That is, the present invention provides an isolation method of ribonucleic acid, which comprises the steps of:

(1) mixing a sample containing a ribonucleic acid, an acidic solution containing a lithium salt and a chaotropic agent and a nucleic acid-binding carrier, to adsorb the ribonucleic acid onto said carrier;

(2) separating the ribonucleic acid-bound carrier from a liquid phase, washing, as necessary, the ribonucleic acid-bound carrier; and (3) eluting the ribonucleic acid from said carrier.

The present invention also provides a reagent for isolating ribonucleic acid, which comprises:

(a) a solution (pH not more than 6.0) for dissolution and adsorption, which contains one or more lithium compounds selected from the group consisting of lithium chloride, lithium acetate, lithium citrate, lithium carbonate, lithium hydroxide and lithium borate and a compound selected from the group consisting of guanidine salt, urea, iodide, perchlorate and (iso)thiocyanate;
(b) a nucleic acid-binding carrier selected from the group consisting of silica, cellulose, nitrocellulose, latex and hydroxyapatite;
(c) a washing solution containing a compound selected from the group consisting of guanidine salt, urea, iodide, perchlorate and (iso)- thiocyanate;
(d) a washing solution which is a buffer having a low salt concentration of not more than 100 mM; and
(e) a solution for eluting ribonucleic acid from the carrier.

Another aspect of the present invention is a method for producing a cDNA, which comprises the steps of:
(1) reacting the ribonucleic acid isolated by the above-mentioned method or the ribonucleic acid-bound carrier used in the above-mentioned method, with a mixture of a reverse transcriptase, a ribonuclease inhibitor, dNTPs, a primer for reverse transcription and a buffer for reverse transcription; and
(2) synthesizing a cDNA from the ribonucleic acid.

According to the present invention, a ribonucleic acid can be isolated from various biological materials quickly and safely with ease and in high yields. The ribonucleic acid obtained by this method can be used suitably for various analyses such as northern blot analysis, RT-PCR analysis and the like.

DETAILED DESCRIPTION OF THE INVENTION

Figure 1:
FIG. 1 shows an agarose gel electrophoresis image of ribonucleic acid isolated from K562 cells by the method of the present invention and the method of Boom et al.

The sample containing a ribonucleic acid in the present invention includes, for example, serum, blood, cerebrospinal fluid, tissue, urine, stool, saliva, semen, cell isolated from a biological material (e.g., blood), cultured cell, and the like. The ribonucleic acid may include, besides the endogenous ribonucleic acid derived from these samples, exogeneous ribonucleic acid derived from virus, bacteria or fungus, ribonucleic acid enzymatically synthesized in vitro and others.

According to the present invention, a sample containing a ribonucleic acid, an acidic solution containing a lithium salt and a chaotropic agent, and a nucleic acid-binding carrier are mixed to bind the ribonucleic acid to said carrier.

The acidic solution containing a lithium salt and a chaotropic agent of the present invention is a solution for dissolution and adsorption of a ribonucleic acid. The lithium salt to be used in the present invention is not subject to any particular limitation as long as it can produce a lithium ion in an aqueous solution. Examples thereof include inorganic lithium salts and organic lithium salts such as lithium chloride, lithium acetate, lithium citrate, lithium carbonate, lithium hydroxide and lithium borate, with particular preference given to lithium chloride. The lithium salt has been confirmed to easily coordinate with ribonucleic acid, as compared with a monovalent cation having a greater ionic radius, such as sodium salt.

A precipitation method for a high molecular weight ribonucleic acid, which uses a lithium ion, has been widely used (Molecular Cloning, 2nd ed., 1.40 (1989)). According to such methods, lithium ion is used to insolubilize ribonucleic acid in a solution, and the insolubilized ribonucleic acid is recovered by centrifugation or filtration. In contrast, it is important in the present invention to adsorb a ribonucleic acid onto a nucleic acid-binding carrier, such as silica, under the conditions that do not insolubilize the ribonucleic acid. In so doing, the presence of a protein denaturing (solubilizing) agent, such as guanidine salt and urea, in a reaction mixture is effective. In fact, in the method of the present invention, a sample is not insolubilized as long as it is in a suitable amount, whereas when it is used in an extremely large amount, coagulation of insolubilized components may occur. In the present invention, therefore, insolubilized ribonucleic acid or other insolubilized components should be removed, or the amount of the sample should be reduced.

By a chaotropic agent is meant a substance capable of changing a secondary, tertiary and/or quaternary structure without exerting an influence on the primary structure of protein and nucleic acid. Examples of the chaotropic agent to be used in the present invention include a compound selected from the group consisting of guanidine salt, urea, iodide, perchlorate and (iso)thiocyanate.

Examples of the guanidine salt to be used in the present invention include inorganic guanidine salt or organic guanidine salt generally used for denaturation of a protein, such as guanidine hydrochloride, guanidine acetate, guanidine phosphate, guanidine (iso)thiocyanate, guanidine sulfate and guanidine carbonate. Two or more from the above-mentioned salts may be combined, where the guanidine salt preferably has a high concentration of not less than 5 M.

Examples of the iodide to be used in the present invention include sodium iodide, potassium iodide and the like, and examples of perchlorate include sodium perchlorate, potassium perchlorate, lithium perchlorate and ammonium perchlorate. The (iso)thiocyanate is exemplified by sodium (iso)thiocyanate, potassium (iso)thiocyanate and ammonium (iso)thiocyanate.

The solution for dissolution and adsorption can contain a surfactant to disrupt plasma membrane and/or solubilize intracellular proteins. The surfactant is subject to no particular limitation as long as it can be generally used to extract a nucleic acid from cells and the like. Specific examples thereof include non-ionic surfactant, such as Triton surfactant and Tween surfactant, and anionic surfactant, such as sodium N-lauroylsarcosinate. In the present invention, a non-ionic surfactant is preferably contained in a proportion of 0.01–0.5%.

For the purpose of protecting the ribonucleic acid from ribonuclease, an antioxidant, such as 2-mercaptoethanol and dithiothreitol, may be added to the solution for dissolution and adsorption.

A certain kind of sample cannot dissolve in the solution for dissolution and adsorption of the present invention. For example, plant, yeast, fungus and certain gram positive bacteria have special cell wall structures, which prevent isolation of ribonucleic acid by the method of the present invention. When a ribonucleic acid is isolated from such a sample, each sample is pretreated (e.g., protoplasted) and then treated by the method of the present invention.

In the present invention, a sample dissolved in the above-mentioned solution for dissolution and adsorption under the acidic condition of not more than pH 6.0 is brought into contact with a nucleic acid-binding carrier, such as silica particles. For this to be achieved, the solution for dissolution and adsorption should be bufferized with a suitable buffer. The buffer used here is subject to no particular limitation as long as it can adjust the pH of the solution for dissolution and adsorption to not more than 6.0. In the present invention, an acetate buffer or citrate buffer having a pH of 3–4 is most preferably used.

The present invention is also characterized by the use of a nucleic acid-binding carrier, such as silica, cellulose, nitrocellulose, latex and hydroxyapatite, which is capable of binding with a ribonucleic acid in the above-mentioned solution for dissolution and adsorption. The term, silica, as used herein includes crystalline silicon dioxide and other silicon oxides, diatomaceous earth, glass powder and chemically modified silica. Said nucleic acid-binding carrier may be, for example, a complex of the above-mentioned substance and a supermagnetic metal oxide. Preferred is a silica carrier containing a supermagnetic metal oxide such as triiron tetroxide. The nucleic acid-binding carrier may have a form of, for example, particle, filter, reaction container and the like, yet is free of particular limitation. Of these, preferred are particles in view of the efficiency of adsorption and elution, wherein the particle size is appropriately determined from the preferable range of 0.05–500 μm according to use.

The ribonucleic acid-bound carrier obtained by the above-mentioned step is isolated from a liquid phase by, for example, removing the liquid phase by filtration or centrifugation. Alternatively, a magnetic field is used to isolate the ribonucleic acid-bound carrier from the liquid phase. When the carrier is a filter or a reaction vessel, the liquid only need be discharged or removed.

The ribonucleic acid-bound carrier obtained by the above-mentioned step is washed by, for example, suspending said ribonucleic acid-bound carrier in a suitable washing solution with, for example, a vortex mixer and isolating the carrier from the liquid phase. The ribonucleic acid-bound carrier is preferably isolated by centrifugation, filtration, column manipulation and the like. A nucleic acid-binding carrier containing a supermagnetic metal oxide in the particles can be easily isolated using a magnet and this mode is most preferable.

The washing solution of the present invention preferably contains a chaotropic agent, preferably a guanidine salt. The concentration of the guanidine salt in the washing solution is preferably not less than 6 M. This solution may contain a surfactant and is free of any particular limitation with regard to its pH.

In the present invention, the ribonucleic acid-bound carrier obtained by washing with a washing solution containing a chaotropic agent, is preferably further washed with a buffer having a low salt concentration. The low salt concentration referred to here means a salt concentration at which level a reverse transcription is not profoundly inhibited when this buffer is present in the final eluate containing the ribonucleic acid, and water is exemplified. In the present invention, a buffer having a concentration of not more than 100 mM is preferably used, with further preference given to Tris buffer, though no limitation is imposed. This solution may contain a surfactant and is free of any particular limitation with regard to pH.

The conventional method using a carrier for isolating nucleic acid uses an organic solvent such as ethanol and acetone at this washing stage, thereby making it necessary to dry the carrier. In contrast, a ribonucleic acid can be eluted without a drying step in the present invention. This is extremely advantageous in shortening the time necessary for the isolation of ribonucleic acid, as well as most preferable when preventing contamination caused by being an open system during drying. The contamination here means cross-contamination between samples and the presence of an amplified nucleic acid in PCR and the like. Such contamination is considered to be most responsible for erroneous judgement in the analytic diagnosis of infections by RT-PCR.

In the elution step of ribonucleic acid in the present invention, a ribonucleic acid is eluted from a nucleic acid-bound carrier onto which the ribonucleic acid has been adsorbed. The eluent to be used for this purpose is not particularly limited as long as it can elute ribonucleic acid from the carrier. Preferable one is Tris-EDTA buffer (10 mM Tris buffer, 1 mM EDTA, pH 8.0). In addition, heating can accelerate the elution. The heating temperature is not particularly limited in the absence of any adverse influence on the ribonucleic acid. Preferred temperature is about 60° C. The ribonucleic acid eluted this way can be directly used for cDNA synthesis using a reverse transcriptase, without desalting or concentration such as dialysis and ethanol precipitation. It can be also used for reverse transcription reaction on the ribonucleic acid-bound carrier, without elution from the carrier.

The method for isolating a ribonucleic acid of the present invention enables efficient isolation of ribonucleic acid from a biological component with less contamination of the deoxyribonucleic acid, by a simple operation without using a harmful solvent, so that it can be undoubtedly used for a ribonucleic acid purification kit and a nucleic acid extraction device which automatically performs preparation of solid phase and dispensing of a reagent. In addition, the ribonucleic acid obtained by the method of the present invention can be used for northern blot analysis, or as a template for the amplification in RT-PCR analysis, NASBA method disclosed in EP 0329822, and the like.

One embodiment of the present invention is a method for isolating a ribonucleic acid, comprising the steps of:
(1) mixing a sample containing the ribonucleic acid, an acidic solution (pH not more than 6.0) containing one or more compounds selected from the group consisting of lithium chloride, lithium acetate, lithium citrate, lithium carbonate, lithium hydroxide and lithium borate, and a compound selected from the group consisting of guanidine salt, urea, iodide, perchlorate and (iso)thiocyanate, and a nucleic acid-binding carrier, particularly a silica carrier, containing a supermagnetic metal oxide, to adsorb the ribonucleic acid onto said carrier;
(2) separating the ribonucleic acid-bound carrier from a liquid phase using a magnetic field;
(3) washing said ribonucleic acid-bound carrier with a washing solution containing a compound selected from the group consisting of guanidine salt, urea, iodide, perchlorate and (iso)thiocyanate and separating said ribonucleic acid-bound carrier using a magnetic field;
(4) washing the carrier with a buffer having a low salt concentration of not more than 100 mM and separating said ribonucleic acid-bound carrier using a magnetic field; and
(5) eluting the ribonucleic acid with a solution capable of separating the ribonucleic acid from said carrier.

The reagent for isolating ribonucleic acid of the present invention includes, for example, (a) a solution (pH not more than 6.0) for dissolution and adsorption of ribonucleic acid, which contains one or more compounds selected from the group consisting of lithium chloride, lithium acetate, lithium citrate, lithium carbonate, lithium hydroxide and lithium borate, and a compound selected from the group consisting of guanidine salt, urea, iodide, perchlorate and (iso) thiocyanate, (b) a nucleic acid-binding carrier selected from the group consisting of silica, cellulose, nitrocellulose, latex and hydroxyapatite, which preferably contains a supermagnetic metal oxide, (c) a washing solution containing a compound selected from the group consisting of guanidine salt, urea, iodide, perchlorate and (iso)thiocyanate, (d) a washing solution which is a buffer having a low salt concentration of not more than 100 mM, and (e) an eluent to elute the ribonucleic acid from said carrier.

The method for producing cDNA of the present invention comprises the steps of (1) reacting the ribonucleic acid isolated by the above-mentioned isolation method or the ribonucleic acid-bound carrier obtained during the above-mentioned isolation method, with a mixture of a reverse transcriptase, ribonuclease inhibitor, dNTPs, a primer for reverse transcription and a buffer for reverse transcription reaction, and (2) synthesizing a cDNA from the ribonucleic acid.

As the reverse transcriptase, AMV reverse transcriptase, M-MLV reverse transcriptase and Tth DNA polymerase can be used. The dNTPs is a mixture of dATP, dCTP, dGTP and dTTP. The primer for reverse transcription can be, for example, a sequence specific primer, oligo-dT primer, random primer or the like. The buffer for reverse transcription reaction contains inorganic salts such as $MgCl_2$, $MnCl_2$ and KCl and has a pH adjusted to make the reverse transcription reaction optimal.

The present invention is described in more detail by way of Examples, which should not be construed as limiting the invention.

Example 1

Extraction of Ribonucleic Acid from Cultured Human Cell (1) Preparation of K562 Cells The cells of human chronic mylogenous leukemia cell line K562 (ATCC, CCL243) were cultured in an RPMI1640 medium (Nissui Seiyaku) containing 10% fetal bovine serum, at 37° C. for 3 days, and centrifuged (1,000 rpm, 5 min) to remove supernatant. The cells were suspended in PBS (−) [137 mM sodium chloride, 2.7 mM potassium chloride, 4.3 mM disodium hydrogenphosphate, 1.4 mM sodium dihydrogenphosphate, pH 7.4). The cells were counted with a hematometer and dispensed in a microtube at $1 \times 10^6$ cells. The supernatant was removed by centrifugation at 1,000 rpm for 5 min to give cell pellets to be used as a sample. The same operation of human promyelotic leukemia cell line HL60 (ATCC, CCL240) gave cell pellets.

(2) Extraction of Ribonucleic Acid (a) To K562 cell and HL60 cell pellets ($1 \times 10^6$ cells) prepared in (1) above in microtubes was respectively added 700 μl of a solution for dissolution and adsorption (6 M guanidine hydrochloride, 1 M lithium chloride, 0.2 M sodium acetate-hydrochloride buffer (pH 3.0), 0.1% Triton X-100, 0.1 M 2-mercaptoethanol) and the cells were completely dissolved. Thereto was added a suspension (20 μl) of magnetic silica particles (0.5 g/ml, particle size 1–10 μm, containing triiron tetraoxide particle by 30%, specific surface area 280 $cm^2/g$, surface pore diameter 2–6 nm, pore volume 0.025 ml/g; manufactured by Suzuki Yushi) in water, and mixed with a vortex mixer at room temperature for 2 min. Then, the microtubes were set on a magnetic stand (MCP-M; manufactured by Dynal) to collect magnetic silica particles. The supernatant was removed with a pipette. The microtubes were removed from the magnetic stand and 1 ml of a washing solution [6 M guanidine hydrochloride, 0.2 M sodium acetate-hydrochloride buffer (pH 4.0)] was added. Using a vortex mixer, the mixture was stirred for about 10 seconds and the microtubes were again set on a magnetic stand to collect magnetic silica particles, followed by removal of supernatant. Then, the particles were washed three times with 10 mM Tris buffer (1 ml, pH 6.4), and the buffer was completely removed. Tris-EDTA buffer (10 mM Tris buffer, 1 mM EDTA, 50 μl, pH 8.0) was added and the magnetic silica particles were suspended by pipetting. Then, the suspension was heated at 60° C. for one minute. The microtubes were again set on a magnetic stand to collect magnetic silica particles, and the supernatant was recovered.

(b) Using said sample and according to the method of Boom et al. (J. Clin. Microbiol., 28(3): 495–503 (1990)), a ribonucleic acid was extracted. A sample, L6 buffer (900 μl, guanidine thiocyanate 120 g, Tris-HCl buffer (pH 6.4) 100 ml, 0.2 M EDTA (pH 8.0) 22 ml, Triton X-100 2.6 g) and a silica particle (manufactured by Sigma) suspension (40 μl) adjusted to 1 g/ml were mixed and stirred at room temperature for 10 minutes. Centrifugation at 12,000×g for 5 minutes removed the supernatant. The precipitates were suspended in an L2 buffer (1 ml, guanidine thiocyanate 120 g, 0.1 M Tris-HCl buffer (pH 6.4) 100 ml), and centrifuged at 12,000×g for 5 minutes to remove the supernatant. This washing step was repeated one more time, and the precipitates were washed twice with 70% ethanol (1 ml) in the same manner. After washing with acetone (1 ml), the precipitates were dried at 56° C. The nucleic acid was eluted with a Tris-EDTA buffer. After heating at 56° C. for 10 minutes, silica particles were precipitated by centrifugation and the supernatant was recovered.

(3) Analysis of Ribonucleic Acid by Agarose Gel Electrophoresis

According to the methods of the present invention and Boom et al., a ribonucleic acid solution (9 μl) obtained from K562 cell and a dye solution (1 μl, 50% glycerol, 0.25% bromophenol blue) were mixed and placed in a slot in a 1% agarose gel. Using a Mupid electrophoresis device (manufactured by Cosmo Bio), the gel was electrophoresed in 1×TBE buffer (89 mM Tris, 89 mM boric acid, 2.5 mM EDTA. 2Na) at 100 V for 30 minutes. After electrophoresis, the gel was immersed in an ethidium bromide solution for 30 minutes, rinsed lightly with tap water and subjected to photographing of the stained gel under UV irradiation using a Polaroid camera. In this method, the deoxyribonucleic acid (genomic DNA) derived from cells and two typical ribonucleic acids (28S rRNA and 18S rRNA) present in cells in comparatively large amounts could be detected. The migration pattern is shown in FIG. 1 wherein lane 1 is a molecular weight marker which was a HindIII digest of λ phage DNA, lane 2 is a ribonucleic acid isolated by the method of the present invention, lane 3 is a ribonucleic acid obtained by the method of Boom et al. As is evident from FIG. 1, the ribonucleic acid (rRNA) obtained by the method of the present invention showed a greater yield than the ribonucleic acid obtained by the method of Boom et al., and less contamination of deoxyribonucleic acid.

(4) Amplification of BCR/abl Fusion mRNA by RT-PCR

Using the ribonucleic acid obtained by the method of the present invention, BCR/abl fusion mRNA specifically expressed in K562 cell was detected by RT-PCR. To ribonucleic acid solutions (each 5 μl) derived from K562 cell and HL60 cell obtained by the method of the present invention were added M-MLV reverse transcriptase (manufactured by TOYOBO), ribonuclease inhibitor (manufactured by TOYOBO), dNTPs, random primer and reaction buffer, to achieve an optimal concentration. Twenty μl thereof was treated at 37° C. for 1 hour and at 95° C. for 5 minutes, and cooled on ice. Then, to a mixture of primers to amplify BCR/abl fusion mRNA sequence, dNTPs, reaction buffer and Taq DNA polymerase (manufactured by TOYOBO) was added 5 μl of the above-mentioned cDNA solution obtained by reverse transcription reaction, to make the total amount 50 μl, and a mineral oil (manufactured by Sigma) was superimposed thereon. Using a DNA Thermal Cycler (manufactured by Perkin Elmer Cetus), a cycle of reactions at 94° C. for 45 seconds, at 55° C. for 45 seconds, and at 72° C. for 1 minute was repeated 30 times.

(5) Detection of Amplification Products by Agarose Gel Electrophoresis

Figure 2:
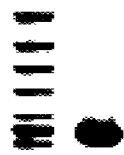
FIG. 2 is an agarose gel electrophoresis image which shows the result of RT-PCR, targeting BCR/abl fusion mRNA, of ribonucleic acids isolated from K562 and HL60 by the present inventive method.

An amplification product (9 μl) and a dye solution (1 μl, 50% glycerol, 0.25% bromophenol blue) were mixed and placed in a slot in a 1.5% agarose gel. Using a Mupid electrophoresis device (manufactured by Cosmo Bio), the gel was electrophoresed in 1×TBE buffer [89 mM Tris, 89 mM boric acid, 2.5 mM EDTA. 2Na] at 100 V for 30 minutes. After electrophoresis, the gel was immersed in an ethidium bromide solution for 30 minutes, rinsed lightly with tap water and subjected to photographing of the stained gel under UV irradiation using a Polaroid camera. As a result, a band corresponding to an amplified fragment derived from BCR/abl fusion mRNA was acknowledged only when RNA extracted from K562 cell was used as a template, and such band was not found in the case of HL60 cell devoid of expression of said gene (FIG. 2). In the migration pattern shown in FIG. 2, lane 1 is a molecular weight marker which was a HincII digest of φX174 phage DNA, lane 2 is an RT-PCR amplification product from ribonucleic acid derived from K562 cell, lane 3 is an RT-PCR amplification product from ribonucleic acid derived from HL60 cell. As is evident from FIG. 2, the method of the present invention enabled isolation of mRNA from cell samples, and the obtained mRNA sufficiently permitted analysis by RT-PCR.

Example 2
Detection of Hepatitis C Virus (HCV) RNA by RT-PCR
(1) Extraction of HCV-RNA from a Serum Serum samples from patients with hepatitis C, which contained 1×10$^5$ copies/ml of HCV, were prepared in a dilution series of 10$^5$, 10$^4$, 10$^3$ and 10$^2$ copies/ml by the use of a normal serum. Each serum sample (100 μl) was used for extraction of HCV-RNA according to the method of Example 1 (2) (a).

(2) Amplification of HCV-RNA by RT-PCR

The HCV-RNA was analyzed by RT-PCR according to the method of Okamoto et al. (J. Exp. Med., 60: 215–222 (1990)). To the solution (5 μl) obtained in (1) were added M-MLV reverse transcriptase (manufactured by TOYOBO), ribonuclease inhibitor (manufactured by TOYOBO), dNTPs, random primer and reaction buffer, to achieve an optimal concentration. Ten μl thereof was treated at 42° C. for 1 hour and at 95° C. for 5 minutes, and cooled on ice. Then, to a mixture of primers to amplify non-coding region of HCV-RNA, dNTPs, reaction buffer and Taq DNA polymerase (manufactured by TOYOBO) was added 2.5 μl of the above-mentioned cDNA solution obtained by reverse transcription reaction, to make the final liquid amount 25 μl, and a mineral oil (manufactured by Sigma) was superimposed thereon. Using a DNA Thermal Cycler (manufactured by Perkin Elmer Cetus), a cycle of reactions at 94° C. for 30 seconds, at 55° C. for 30 seconds, and at 72° C. for 1 minute was repeated 30 times. Then, the amplification product (1 μl) obtained by these reactions was again amplified by 30 cycles of PCR using inner primers; 2 step PCR.

(3) Detection of Amplified DNA with Agarose Gel Electrophoresis

Figure 3:
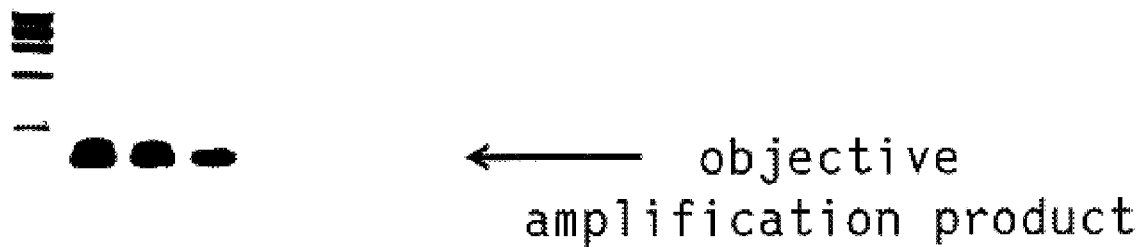
FIG. 3 is an electrophoresis image which shows the result of RT-PCR analysis of HCV RNA isolated from a serum by the present inventive method.

An amplification product (9 μl) and a dye solution (1 μl, 50% glycerol, 0.25% bromophenol blue) were mixed and placed in a slot in a 1.5% agarose gel. Using a Mupid electrophoresis device (manufactured by Cosmo Bio), the gel was electrophoresed in 1×TBE buffer (89 mM Tris, 89 mM boric acid, 2.5 mM EDTA. 2Na) at 100 V for 30 minutes. After electrophoresis, the gel was immersed in an ethidium bromide solution for 30 minutes, lightly rinsed with tap water and subjected to photographing of the stained gel under UV irradiation using a Polaroid camera. As a result, a specific amplification band was detected up to a serum of 10$^3$ copies/ml, and ribonucleic acid derived from virus was efficiently isolated, which suggested possible analysis by RT-PCR (FIG. 3). In FIG. 3, lane 1 is a molecular weight marker which was a HaeIII digest of φX174 phage DNA, lanes 2–5 are RT-PCR amplification products using ribonucleic acids extracted from sera respectively containing 10$^5$, 10$^4$, 10$^3$ and 10$^2$ copies/ml HCV as templates, lane 6 is an RT-PCR amplification product obtained using ribonucleic acid extracted from normal serum as a template.

Example 3
Extraction of Ribonucleic Acid Using Solutions for Dissolution and Adsorption Having Various Compositions Using solutions for dissolution and adsorption having various compositions shown in Table 1 below and in the same manner as in Example 1 (2)(a), nucleic acid was extracted from K562 cell line (2×10$^6$ cells). Each extract was subjected to agarose gel electrophoresis and the intensity of the band was evaluated in three levels, the results of which are shown in Table 1. In Table 1, the number of "+" shows the level of intensity of the band, wherein greater numbers of "+" mean more intensive bands, "−" means that a band was not detectable, GuHCl is guanidine hydrochloride, and GUSCN is guanidine thiocyanate.

TABLE 1

| No. | solution for dissolution and adsorption | 28S rRNA | 18S rRNA | Genomic DNA |
|---|---|---|---|---|
| 1 | 5M GuHCl, 1.5M LiCl, 0.2M NaOAc-HCl (pH 3.0) | +++ | +++ | − |
| 2 | 5M GuHCl, 0.2M NaOAc-HCl (pH 3.0) | ++ | ++ | + |
| 3 | 5M GuHCl, 1.5M LiCl, 0.2M Tris-HCl (pH 6.5) | − | − | +++ |
| 4 | 5M GuHCl, 0.2M Tris-HCl (pH 6.5) | − | − | +++ |
| 5 | 5M GuSCN, 1.5M LiCl, 0.2M NaOAc-HCl (pH 4.0) | +++ | +++ | − |
| 6 | 5M GuSCN, 0.2M NaOAc-HCl (pH 4.0) | ++ | ++ | + |
| 7 | 5M GuSCN, 1.5M LiCl, 0.2M Tris-HCl (pH 6.5) | − | − | +++ |
| 8 | 5M GuSCN, 0.2M Tris-HCl (pH 6.5) | − | − | +++ |

The results indicate that an acidic solution for dissolution and adsorption which contained a lithium salt and a chaotropic agent noticeably improved selectivity of the nucleic acid-binding carrier for RNA adsorption to result in greater RNA yields.

This application is based on application No. 183381/1996 filed in Japan, the content of which is incorporated hereinto by reference.

What is claimed is:

1. A method for isolating a ribonucleic acid, comprising the steps of:
   (1) mixing a sample containing the ribonucleic acid, an acidic solution containing a lithium salt and a chaotropic agent, and a nucleic acid-binding carrier, to absorb the ribonucleic acid onto said carrier to form a ribonucleic acid-bound carrier;
   (2) isolating the ribonucleic acid-bound carrier from a liquid phase; and
   (3) eluting the ribonucleic acid from said carrier in order to obtain substantially isolated ribonucleic acid.

2. The method for isolating a ribonucleic acid according to claim 1, wherein the chaotropic agent is selected from the group consisting of guanidine salt, urea, iodide, perchlorate and (iso)thiocyanate.

3. The method for isolating a ribonucleic acid according to claim 2, wherein said guanidine salt is a member selected from the group consisting of guanidine hydrochloride, guanidine acetate, guanidine phosphate, guanidine (iso) thiocyanate, guanidine sulfate and guanidine carbonate.

4. The method for isolating a ribonucleic acid according to claim 2, wherein said iodide is a member selected from the group consisting of sodium iodide and potassium iodide.

5. The method for isolating a ribonucleic acid according to claim 2, wherein said perchlorate is a member selected from the group consisting of sodium perchlorate, potassium perchlorate, lithium perchlorate and ammonium perchlorate.

6. The method for isolating a ribonucleic acid according to claim 2, wherein said (iso)thiocyanate is a member selected from the group consisting of sodium (iso) thiocyanate, potassium (iso)thiocyanate and ammonium (iso)thiocyanate.

7. The method for isolating a ribonucleic acid according to claim 1, wherein said sample containing the ribonucleic acid is a member selected from the group consisting of serum, blood, tissue, urine, stool, saliva, cell isolated from a biological material and cultured cell.

8. The method for isolating a ribonucleic acid according to claim 1, wherein said lithium salt is an inorganic lithium salt or an organic lithium salt.

9. The method for isolating a ribonucleic acid according to claim 1, wherein said lithium salt is at least one member selected from the group consisting of lithium chloride, lithium acetate, lithium citrate, lithium carbonate, lithium hydroxide and lithium borate.

10. The method for isolating a ribonucleic acid according to claim 1, wherein said acidic solution has a pH of not more than 6.0.

11. The method for isolating a ribonucleic acid according to claim 1, wherein said nucleic acid-binding carrier contains silica.

12. The method for isolating a ribonucleic acid according to claim 1, wherein said nucleic acid-binding carrier is a particle.

13. The method for isolating a ribonucleic acid according to claim 1, wherein said nucleic acid-binding carrier contains a supermagnetic metal oxide.

14. The method for isolating a ribonucleic acid according to claim 1, further comprising a step of washing said ribonucleic acid-bound carrier with a washing solution, after isolation of said ribonucleic acid-bound carrier from the liquid phase.

15. The method for isolating a ribonucleic acid according to claim 1, further comprising a step of washing said ribonucleic acid-bound carrier with a washing solution containing a chaotropic agent, after isolation of said ribonucleic acid-bound carrier from the liquid phase.

16. The method for isolating a ribonucleic acid according to claim 15, further comprising a step of washing the ribonucleic acid-bound carrier with a buffer having a low salt concentration, after washing the carrier with the washing solution containing the chaotropic agent.

17. The method for isolating a ribonucleic acid according to claim 16, wherein said buffer has a salt concentration of not more than 100 mM.

18. The method for isolating a ribonucleic acid according to claim 16, further comprising a step of eluting the ribonucleic acid using a solution capable of eluting the ribonucleic acid, from the ribonucleic acid-bound carrier, after washing the carrier with the buffer.

19. The method for isolating a ribonucleic acid according to claim 1, wherein the ribonucleic acid is eluted from the ribonucleic acid-bound carrier by heating the carrier.

20. The method for isolating a ribonucleic acid according to claim 1, wherein the nucleic acid-binding carrier contains a supermagnetic metal oxide, and the carrier carrying the ribonucleic acid is isolated from the liquid phase using an isolation magnetic field.

21. A method for isolating a ribonucleic acid, comprising the steps of:
   (1) mixing a sample containing the ribonucleic acid, an acidic solution containing a lithium salt and a guanidine salt or urea, and a nucleic acid-binding carrier, to allow adsorption of the ribonucleic acid onto said carrier to form a ribonucleic acid-bound carrier;
   (2) isolating the ribonucleic acid-bound carrier from a liquid phase; and
   (3) eluting the ribonucleic acid from the ribonucleic acid-bound carrier in order to obtain substantially isolated ribonucleic acid.

22. A method for isolating a ribonucleic acid, comprising the steps of:
   (1) mixing a sample containing the ribonucleic acid, an acidic solution of a pH not more than 6 and containing one or more lithium compounds selected from the group consisting of lithium chloride, lithium acetate, lithium citrate, lithium carbonate, lithium hydroxide, and lithium borate, and a chaotropic agent selected from the group consisting of guanidine salt, urea, iodide, perchlorate and (iso)thiocyanate, and a nucleic acid-binding carrier containing a supermagnetic metal oxide, to adsorb the ribonucleic acid onto said carrier to form a ribonucleic acid-bound carrier;
   (2) separating the ribonucleic acid-bound carrier from a liquid phase using a magnetic field;
   (3) washing said ribonucleic acid-bound carrier with a washing solution containing a chaotropic agent selected from the group consisting of guanidine salt, urea, iodide, perchlorate and (iso)thiocyanate and separating said ribonucleic acid-bound carrier using a magnetic field;
   (4) washing the carrier with a buffer having a low salt concentration of not more than 100 mM and separating said ribonucleic acid-bound carrier using a magnetic field; and
   (5) eluting the ribonucleic acid with a solution capable of separating the ribonucleic acid from said carrier in order to obtain substantially isolated ribonucleic acid.

23. A reagent for isolating a ribonucleic acid, which comprises:
   (a) a solution (pH not more than 6.0) for dissolution and adsorption, which contains one or more lithium compounds selected from the group consisting of lithium chloride, lithium acetate, lithium citrate, lithium carbonate, lithium hydroxide and lithium borate and a chaotropic agent selected from the group consisting of guanidine salt, urea, iodide, perchlorate and (iso)thiocyanate;

(b) a nucleic acid-binding carrier selected from the group consisting of silica, cellulose, nitrocellulose, latex and hydroxyapatite;

(c) a washing solution containing a chaotropic agent selected from the group consisting of guanidine salt, urea, iodide, perchlorate and (iso)thiocyanate;

(d) a washing solution which is a buffer having a low salt concentration of not more than 100 mM; and (e) a solution for eluting the ribonucleic acid from the carrier.

24. The reagent for isolating a ribonucleic acid according to claim 23, wherein said nucleic acid-binding carrier contains a supermagnetic metal oxide.

25. A method for producing a cDNA, comprising reacting a ribonucleic acid isolated according to the method of claim 1, with a mixture of a reverse transcriptase, a ribonuclease inhibitor, dNTPs, a primer for reverse transcription and a buffer for reverse transcription reaction, and synthesizing the cDNA from the ribonucleic acid in order to obtain a cDNA.

26. A method for producing a cDNA, comprising reacting a ribonucleic acid-bound carrier obtained by the method of claim 1, with a mixture of a reverse transcriptase, a ribonuclease inhibitor, dNTPs, a primer for reverse transcription and a buffer for the reverse transcription reaction, and synthesizing the cDNA from the ribonucleic acid in order to obtain a cDNA.

* * * * *